United States Patent [19]
Brown

[11] Patent Number: 5,459,769
[45] Date of Patent: Oct. 17, 1995

[54] PROCEDURE FOR MONITORING CONTRAST AGENT APPLICATION IN A CT IMAGING SYSTEM

[75] Inventor: Barry D. Brown, Pewaukee, Wis.

[73] Assignee: General Electric Company, Milwaukee, Wis.

[21] Appl. No.: 336,818

[22] Filed: Nov. 9, 1994

[51] Int. Cl.$^6$ .......................... A61B 6/03; G01N 23/083
[52] U.S. Cl. .................................. 378/4; 378/8; 378/16; 378/901
[58] Field of Search .............................. 378/4, 8, 16, 98, 378/98.2, 98.9, 98.12, 901

[56] References Cited

U.S. PATENT DOCUMENTS

| | | | |
|---|---|---|---|
| 4,477,923 | 11/1984 | Baumann et al. | 378/95 |
| 4,672,651 | 6/1987 | Horiba et al. | 378/62 |
| 5,018,173 | 5/1991 | Komai et al. | 378/4 |
| 5,383,231 | 1/1995 | Yamagishi | 378/15 |

OTHER PUBLICATIONS

*Fast Digital Recording of X-Ray Dilution Curves: A Preliminary Evaluation*, Radiology 145:545–547, Nov. 1982, K. H. Hubener, M.D., et al.
*Bolus Geometry and Dynamics after Intravenous Contrast Medium Injection*, Radiology 1984; 153:365–368, Claussen, M.D., et al.

Primary Examiner—Paul M. Dzierzynski
Assistant Examiner—David Vernon Bruce
Attorney, Agent, or Firm—Quarles & Brady

[57] ABSTRACT

In a CT imaging system a baseline image is acquired prior to the injection of a contrast agent into the subject and a series of monitoring images are acquired which enable the affects of the contrast agent to be observed in real time. Regions in the baseline image may be selected with a cursor and the contrast enhancement amounts in these regions are calculated and displayed in both graphic and numerical form. By observing the changes that occur in the displayed information, the operator can determine the moment to begin the image scan for optimal image contrast.

10 Claims, 3 Drawing Sheets

PROCEDURE FOR MONITORING CONTRAST AGENT APPLICATION IN A CT IMAGING SYSTEM

BACKGROUND OF THE INVENTION

The present invention relates to computed tomography (CT) imaging apparatus; and more particularly, to the use of contrast agents with such apparatus.

In a contemporary computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

The clinical value of an x-ray image resides in the contrast produced by differences in x-ray attenuation. Such differences are quite pronounced in some cases, such as bone versus surrounding soft tissues, but in others, the attenuation difference between adjacent tissues is very small. To enhance image contrast, a contrast agent may be intravenously administered to the patient prior to the scan. In dynamic liver studies, for example, the contrast agent helps to differentiate abnormal tissue from the surrounding normal tissue by increasing their x-ray attenuation difference. The resulting enhancement, when a contrast agent is injected, is a dynamic process, and the timing of the image scanning relative to the timing of this enhancement is critical to the diagnostic value of the study.

When a contrast agent is injected in a patient during a liver study, for example, the x-ray contrast goes through three circulation phases. The initial "bolus" phase lasts about 60 to 90 seconds while the contrast agent is being injected. In a dynamic liver study for example, vascular attenuation increases and is much greater than hepatic parenchymal attenuation in this phase. The next phase, called "non-equilibrium", lasts for another 60 to 90 seconds. During this phase, vascular attenuation decreases until it equals hepatic parenchymal attenuation. The "equilibrium" phase is reached once the vascular and parenchymal attenuations can no longer be differentiated on the basis of their x-ray attenuation characteristic.

Dynamic CT exams take advantage of the non-equilibrium phase by acquiring x-ray attenuation data for images when the attenuation differences are at a maximum. In a liver study, for example, during the non-equilibrium phase the hypovascular hepatic metastases appear darker than the surrounding parenchyma in an x-ray image. Since the non-equilibrium phase is short, it is important to start the exam at the optimal moment. Doctors and technologists rely on past experience and general medical knowledge to know when optimal contrast enhancement will be achieved in a given patient. They must take many things into consideration, like the patient's weight and hydration state and the patient's cardiac output. Other variables include contrast agent concentration and its rate of injection. Some clinical sites routinely perform "trial" contrast injection exams on patients before the prescribed diagnostic exam just to determine when optimal contrast enhancement will be achieved in the target tissues of those patients.

In some studies, such as vascular and perivascular studies, the use of contrast agents takes advantage of the bolus phase. Optimal contrast enhancement will happen very early after contrast agent injection begins (6–50 seconds after injection depending on the anatomy under study). If the exam is started too early, the first images will not have enough enhancement. If started too late, surrounding tissue will already be highlighted and can not be distinguished from the vascular structures under study.

Studies using contrast agents are often less than optimal because the scans miss the optimal contrast window for the type of study being performed. Doctors need a tool which will enable them to see when the optimal contrast level has been reached in the patient so that the exam can be started when it will produce the best images possible.

SUMMARY OF THE INVENTION

The present invention is an improved x-ray CT imaging system in which the application of a contrast agent to a patient is monitored and information is displayed to the operator which enables him to determine when the desired image contrast enhancement is achieved in the target tissues. More specifically, the invention includes: performing a baseline scan of target tissues in a patient using the x-ray CT system, displaying a baseline image reconstructed with data acquired in the baseline scan; selecting a region in the baseline image to be monitored; and performing a monitoring operation after injection of a contrast agent in the patient which includes, performing a monitor scan of the target tissues, displaying a monitor image reconstructed from data acquired in the monitor scan, calculating a contrast enhancement amount using attenuation values in the monitor image in the selected region, and displaying the contrast enhancement amount; and wherein the monitoring operation is performed repeatedly until an image scan is commenced.

A general object of the invention is to provide the CT system operator with information that will enable a scan using contrast agents to be performed with maximum effectiveness. The monitor image of the target tissues is continuously updated after injection of the contrast agent to provide a real-time indication of its affect on image contrast. In addition, the contrast enhancement calculation is continuously made on tissues within the selected region and is provided in a form such as a graph or column of numbers which indicates to the operator which phase (i.e. bolus, non-equilibrium or equilibrium) the dynamic study is in. With this information the operator can decide the opportune moment when the image scan should be started to obtain the desired image contrast.

DESCRIPTION OF THE PREFERRED EMBODIMENT

Figure 1:
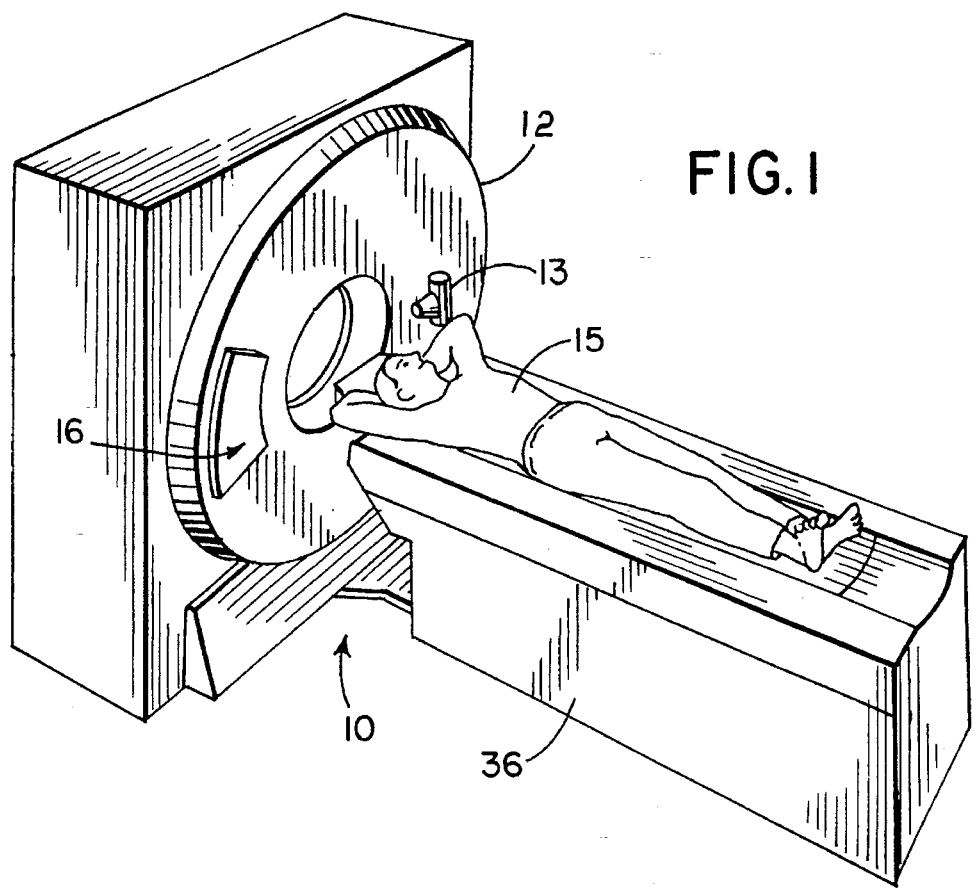
FIG. 1 is a pictorial view of a CT imaging system in which the present invention may be employed.
Figure 2:
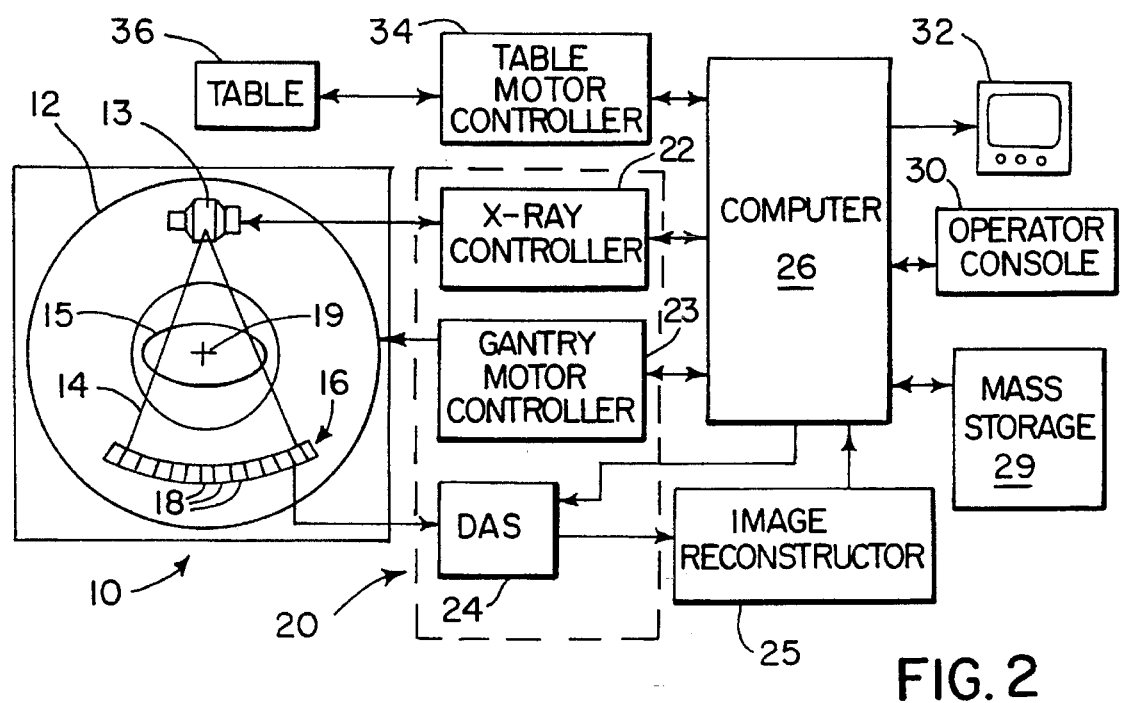
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction. The reconstructed image is applied as an input to a computer 26 which produces a display as will be described in more detail below, or stores the image in a mass storage device 29.

The computer 26 also receives commands and scanning parameters from an operator via console 30 that has a keyboard and touch panel. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

The present invention is implemented on this CT imaging system as a set of programs executed by the computer 26. The operation of the CT system under the direction of these programs is depicted by the flow chart in FIG. 3.

The procedure begins by performing a scout scan as indicated by process block 100. As is well known in the art, in a scout scan the gantry 12 does not rotate and the patient table 36 is translated so that a single projection view is acquired at slice locations along the entire axial extent of the region of interest. From the resulting image, the operator can prescribe the particular scan parameters that will be used, such as the number of slices, their thickness, their location and the x-ray dose. As will be described in more detail below, at this time the operator also selects a number of other parameters such as monitor delay, monitor scan delay, scan delay, and a contrast enhancement threshold value CT.

Figure 4:
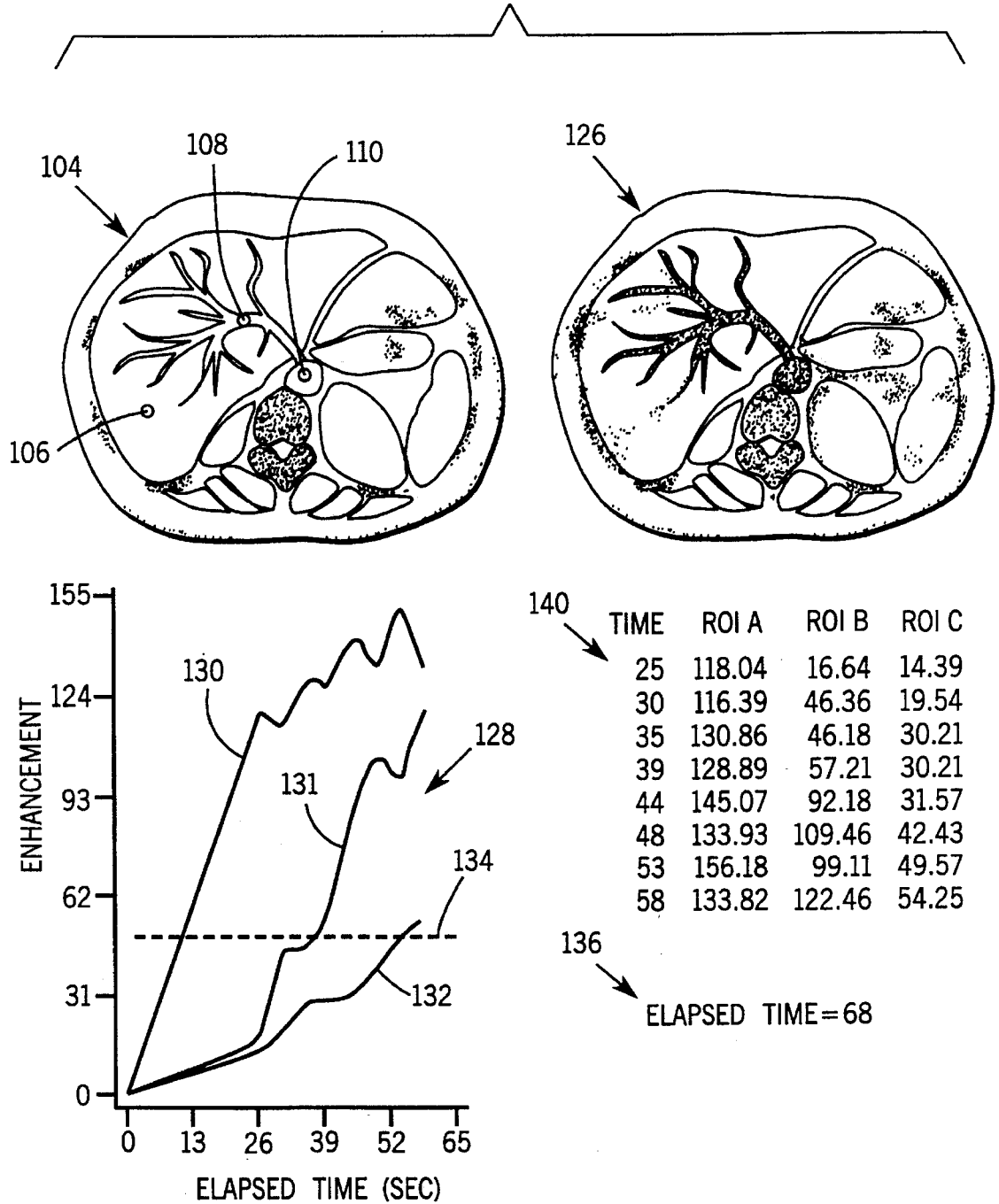
FIG. 4 is a display which is produced by the CT imaging system while carrying out the preferred embodiment of the invention.

As indicated by process block 102, the next step in the procedure is to perform a baseline scan at the location where contrast enhancement is to be observed. The baseline scan is a low-dose, half-scan in which the x-ray tube ma is reduced to one third or less of a typical scan and views are acquired through one half revolution of the gantry 12 (plus the fan beam angle). The x-ray dose is thus considerably less than a normal image scan, but nevertheless, a slice image may be reconstructed. This reconstructed slice image 104 is displayed on the CRT 32 as shown in FIG. 4. The operator may then select from one to three measurement regions (A, B and C) by moving three elliptical cursors 106, 108 and 110 to locations in the baseline image 104. These regions will be quantitatively monitored for changes in contrast enhancement. In a liver scan, as illustrated in FIG. 4 for example, the cursor 106 may be located over the aorta artery, the cursor 108 may be located over the portal vein in the liver, and the cursor 110 may be located over the liver tissue containing the suspected abnormality. The mean value of the CT numbers in each of these regions A, B and C is then calculated, and these form baseline contrast enhancement values $C_A$, $C_B$ and $C_C$.

Referring again to FIG. 3, the system then waits for the patient to be injected with the contrast agent as indicated at decision block 116. When the operator signals that this event has occurred, a real time clock (not shown) is started and the system branches to a prescribed delay period indicated at process block 118. This is manually selected from 3 to 90 seconds to allow time for the contrast agent to begin reaching the monitored region of interest. When this delay time expires, a loop is entered in which a monitor scan is performed and a monitor image reconstructed as indicated at process block 120. The monitor scan is virtually identical to the baseline scan described above in that it is a low dose half-scan from which an image can be reconstructed. As indicated at process block 122, the mean value of the CT numbers in each of the selected monitor regions A, B and C of this image are then calculated, and the corresponding baseline attenuation values $C_A$, $C_B$ and $C_C$ are subtracted from them to determine the amount of contrast enhancement that has occurred.

Figure 3:
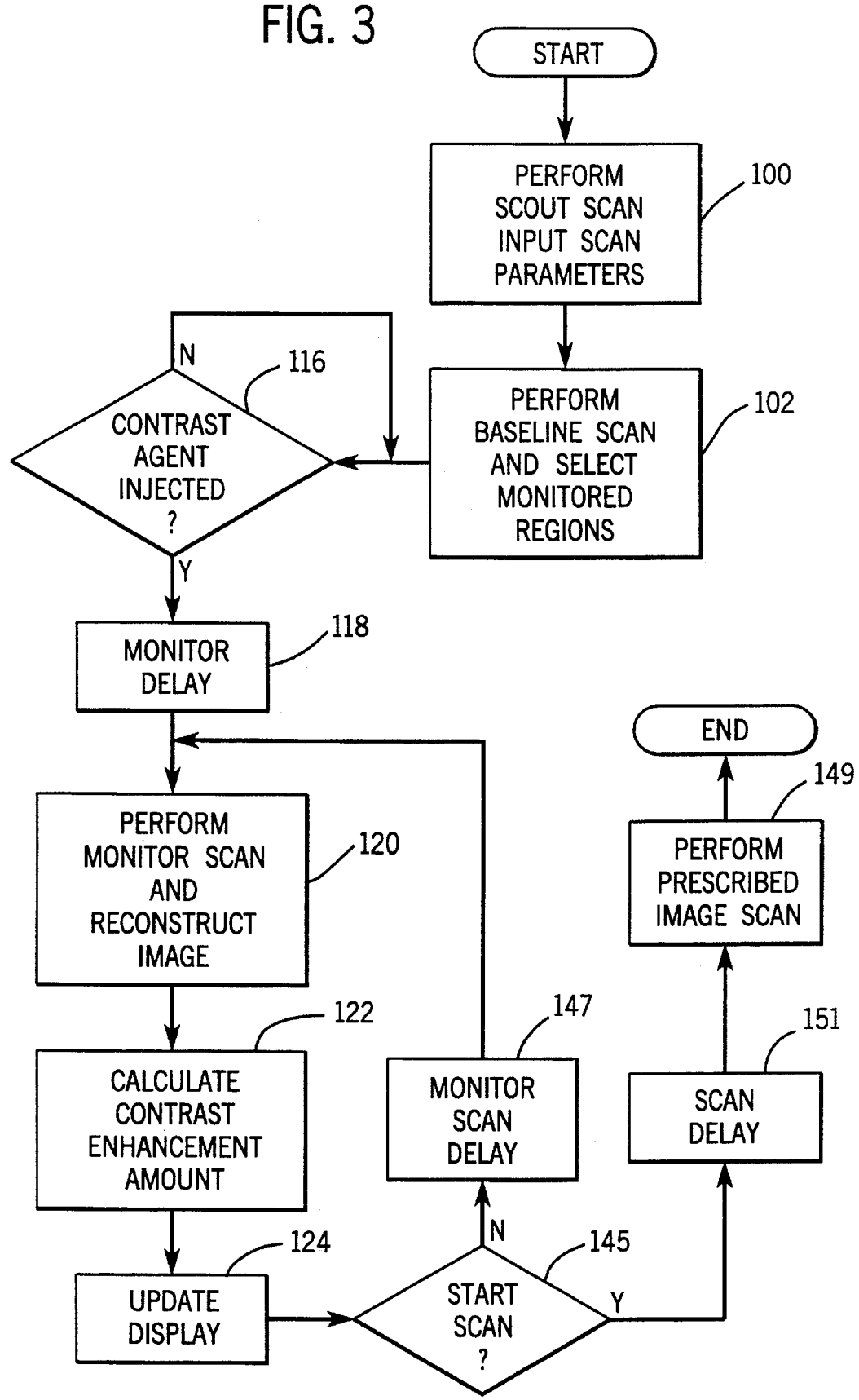
FIG. 3 is a flow chart of the procedure carried out by the CT image system according to the present invention.

Referring particularly to FIGS. 3 and 4, the CRT display is then updated as indicated by process block 124. This update includes displaying the most recent monitor image 126 alongside the baseline image 104 so that the operator can see the change in image contrast taking place as the monitor phase continues. Also, a graphic display 128 is updated. This graph plots the contrast enhancement amounts (in Houndsfield units) as a function of time. As a result, up to three separate graphs 130, 131 and 132 are displayed showing the changes in mean CT values in each of the selected regions A, B and C since the injection of the contrast agent. The prescribed contrast enhancement threshold CT is also shown on this graphic display 128, as indicated by dashed line 134. This enables the operator to visually compare the measured contrast enhancement with this prescribed target level. The current value of the real time clock is also displayed at 136. This provides an indication of elapsed time since the injection of the contrast agent.

And finally, the updated display contains a table 140 which lists in three columns the measured contrast enhancement values for each selected region A, B and C. In the preferred embodiment, up to ten successive monitor images and associated sets of contrast enhancement values may be produced while in the monitor phase. The table 140 thus provides space for ten entries in each column, and the graph 128 provides ten points along the time axis.

Referring particularly to FIG. 3, the monitor phase of the procedure continues until the operator manually starts the scan, as indicated at decision block 145, or ten monitor images have been acquired. If the monitor phase is to continue, a prescribed delay indicated at process block 147 occurs before looping back to perform another monitor scan at process block 120. This delay is prescribed by the operator when the scan parameters are set at process block 100, and it determines the size of the increments of time (e.g. 3 to 90 seconds) along the time axis of the graphic display 128.

When the monitoring phase ends as determined at decision block 145, the prescribed image scan(s) is performed as indicated by process block 149 after a prescribed time delay 151. The time delay 151 enables the CT imaging system to move from its monitoring orientation to the orientation required to begin the scan, and it provides time for the patient to initiate a breath hold.

When the present invention was applied to image the liver, for example, the actual time delays which produce optimal image contrast ranged from 57 to 86 seconds. When the invention is not used, the practice is to delay the examination 60 or 70 seconds for all patients. The invention allows consistent enhancement of liver images from individual to individual, as well as standardizing the examination of individuals having repeated examinations.

I claim:

1. A method for performing a scan with a CT imaging system using a contrast agent which is injected into a subject to enhance image contrast, the steps comprising:

performing a baseline scan of the subject with the CT imaging system;

displaying a baseline image reconstructed with data acquired in the baseline scan;

selecting a region in the baseline image to be monitored;

performing a monitoring operation after injection of the contrast agent into the subject which includes:
 a) performing a monitor scan of the subject;
 b) displaying a monitor image reconstructed from data acquired in the monitor scan;
 c) calculating a contrast enhancement amount using attenuation values in the monitor image from the selected region;
 d) displaying the contrast enhancement amount; and
 e) repeating steps a) through d) until an indication that the image scan should begin is received; and performing an image scan and reconstructing the contrast enhanced image.

2. The method as recited in claim 1 in which a plurality of regions in the baseline image are selected to be monitored and the contrast enhancement amount for each selected region is calculated in step c) and displayed in step d).

3. The method as recited in claim 1 in which the contrast enhancement amount is displayed in a graph.

4. The method as recited in claim 3 in which the contrast enhancement amount is also displayed in numerical form.

5. The method as recited in claim 1 in which the contrast enhancement amount is calculated in step c) by determining the mean value of the attenuation values within the selected region of the monitor image and subtracting therefrom the mean value of the attenuation values within the corresponding selected region of the baseline image.

6. The method as recited in claim 1 in which a contrast enhancement threshold is selected and is displayed in step d).

7. The method as recited in claim 6 in which the contrast enhancement amount is displayed in a graph, and the contrast enhancement threshold is also displayed in said graph.

8. The method as recited in claim 1 in which the baseline scan and the monitor scan are low x-ray dose scans.

9. The method as recited in claim 8 in which the baseline scan and the monitor scan are half scans in which a gantry on the CT imaging system revolves less than a full revolution during the scans.

10. The method as recited in claim 1 which includes displaying the total elapsed time since the injection of the contrast agent into the subject.

* * * * *